United States Patent
Zhang

(10) Patent No.: US 12,383,122 B2
(45) Date of Patent: Aug. 12, 2025

(54) DISPOSABLE UTERINE ENDOSCOPE

(71) Applicant: JIANGSU JIYUAN MEDICAL TECHNOLOGY CO., LTD, Jiangsu (CN)

(72) Inventor: Yunfei Zhang, Jiangsu (CN)

(73) Assignee: JIANGSU JIYUAN MEDICAL TECHNOLOGY CO., LTD, Jiangsu (CN)

( * ) Notice: Subject to any disclaimer, the term of this patent is extended or adjusted under 35 U.S.C. 154(b) by 531 days.

(21) Appl. No.: 17/794,260

(22) PCT Filed: Jun. 8, 2021

(86) PCT No.: PCT/CN2021/098756
§ 371 (c)(1),
(2) Date: Jul. 21, 2022

(87) PCT Pub. No.: WO2022/001591
PCT Pub. Date: Jan. 6, 2022

(65) Prior Publication Data
US 2023/0048570 A1     Feb. 16, 2023

(30) Foreign Application Priority Data
Dec. 9, 2020   (CN) .......................... 202011447980.1

(51) Int. Cl.
*A61B 1/00*     (2006.01)
*A61B 1/005*    (2006.01)
(Continued)

(52) U.S. Cl.
CPC ...... *A61B 1/00103* (2013.01); *A61B 1/00042* (2022.02); *A61B 1/00068* (2013.01);
(Continued)

(58) Field of Classification Search
CPC . A61B 1/00066; A61B 1/00068; A61B 1/015; A61B 1/00183; A61B 1/0055
See application file for complete search history.

(56) References Cited

U.S. PATENT DOCUMENTS

| | | | |
|---|---|---|---|
| 2011/0077678 A1 | 3/2011 | Ryan et al. | |
| 2011/0112365 A1* | 5/2011 | Galperin | G02B 23/2476 600/118 |

(Continued)

FOREIGN PATENT DOCUMENTS

| | | |
|---|---|---|
| CN | 110151103 | 8/2019 |
| CN | 111184499 | 5/2020 |

(Continued)

OTHER PUBLICATIONS

"International Search Report (Form PCT/ISA/210) of PCT/CN2021/098756," mailed on Aug. 27, 2021, with English translation thereof, pp. 1-5.

*Primary Examiner* — Alexandra L Newton
(74) *Attorney, Agent, or Firm* — JCIPRNET

(57) ABSTRACT

A disposable uterine endoscope relates to the technical field of medical instruments. The disposable uterine endoscope includes a handle mechanism and an intubation mechanism. The intubation mechanism includes a rotary inner tube and a supporting outer tube. One end of the rotary inner tube is rotatably connected with the handle mechanism and the other end of the rotary inner tube is connected with a camera. The supporting outer tube is sleeved in a circumferential direction of the rotary inner tube, one end of the supporting outer tube is fixedly connected with the handle mechanism and the other end of the supporting outer tube is provided with a bent section, the bent section is provided with a continuous bent groove, and the bent groove is arranged spirally along the circumferential direction of the bent section.

8 Claims, 8 Drawing Sheets

(51) Int. Cl.
  *A61B 1/015* (2006.01)
  *A61B 1/05* (2006.01)
  *A61B 1/06* (2006.01)
  *A61B 1/12* (2006.01)
  *A61B 1/303* (2006.01)

(52) U.S. Cl.
  CPC ...... *A61B 1/00105* (2013.01); *A61B 1/00114* (2013.01); *A61B 1/00137* (2013.01); *A61B 1/00147* (2013.01); *A61B 1/0055* (2013.01); *A61B 1/015* (2013.01); *A61B 1/05* (2013.01); *A61B 1/0676* (2013.01); *A61B 1/0684* (2013.01); *A61B 1/126* (2013.01); *A61B 1/303* (2013.01)

(56) References Cited

U.S. PATENT DOCUMENTS

2019/0298321 A1* 10/2019 Intintoli ............... A61B 1/07
2022/0142463 A1* 5/2022 Altshuler ............. A61B 1/018

FOREIGN PATENT DOCUMENTS

| CN | 111603132 | 9/2020 |
| CN | 211609713 | 10/2020 |
| CN | 112472016 | 3/2021 |

* cited by examiner

DISPOSABLE UTERINE ENDOSCOPE

CROSS-REFERENCE TO RELATED APPLICATION

This application is a 371 of international application of PCT application serial no. PCT/CN2021/098756, filed on Jun. 8, 2021, which claims the priority benefit of China application no. 202011447980.1, filed on Dec. 9, 2020. The entirety of each of the above mentioned patent applications is hereby incorporated by reference herein and made a part of this specification.

TECHNICAL FIELD

The application relates to the field of medical apparatus and instruments, in particular to a disposable uterine endoscope.

BACKGROUND

At present, the uterine endoscope, also known as an uteroscope, is a novel minimally invasive gynecologic diagnosis and treatment technology. A fiber light source endoscope for examination and treatment in uterine cavity includes an uteroscope, an energy source system, a light source system, a perfusion system and an imaging system. A front portion of the endoscope body enters the uterine cavity to have an amplifying effect to an observed part, so that the uterine endoscope becomes a first choice examination method for gynecologic hemorrhagic disorders and intra-uterine lesions intuitively and accurately.

The uterine endoscope in the related technology includes a handheld handle mechanism and an intubation mechanism inserted into the uterus. The intubation mechanism includes a rotary inner tube and a supporting outer tube. The supporting outer tube is arranged on the periphery of the rotary inner tube in a sleeving manner. One end of the rotary inner tube is rotatably connected with the handle mechanism and the other end of the rotary inner tube is connected with a camera, and the side of the rotary inner tube provided with the camera is inserted into the uterus through a vagina. As the uterus is connected with a fallopian tube, in order to be adaptive to the shape of a connection between the fallopian tube and the uterus, generally, the side of the rotary inner tube provided with the camera is bended. One end of the supporting outer tube is fixedly connected with the handle mechanism and the other end thereof extends to the side of the rotary inner tube provided with the camera. A straight line section of the supporting outer tube is kept immobile when the rotary inner tube rotates. In order that a bent section of the supporting outer tube follows when the bent portion of the supporting inner tube rotates, the supporting outer tube and the rotary inner tube are both made from medical stainless steel. The bent section of the supporting outer tube is provided with a continuous thread, so that the bent section of the supporting outer tube twists as the rotary inner tube rotates.

SUMMARY

Technical Problem

Aiming at the related technology, the inventor believes that the bent section of the supporting outer tube is provided with the thread, which facilitates twisting of the supporting outer tube. At the moment, when the bent section is stressed, one section only has two points to stress, so that it is easy to reduce the strength of the supporting outer tube. When the rotary inner tube is rotated frequently, the supporting outer tube is easy to break as the bent section of the supporting outer tube twists frequently. If the broken bent section falls into the uterus, medical hidden dangers are easily caused.

Problem to Solve

Technical Solution

In order to improve the problem that the bent section of the supporting outer tube is easily broken in the uterus, the application provides a disposable uterine endoscope.

The disposable uterine endoscope provided by the application adopts a technical scheme below:

A disposable uterine endoscope, including a handle mechanism and an intubation mechanism, wherein the intubation mechanism includes a rotary inner tube and a supporting outer tube, and one end of the rotary inner tube is rotatably connected with the handle mechanism and the other end of the rotary inner tube is connected with a camera; the supporting outer tube is sleeved in a circumferential direction of the rotary inner tube, one end of the supporting outer tube is fixedly connected with the handle mechanism and the other end of the supporting outer tube is provided with a bent section; and wherein the bent section is provided with a continuous bent groove, and the bent groove is arranged spirally along the circumferential direction of the bent section.

By adopting the technical scheme, by arranging the continuous bent groove, the application has an effect of reducing the medical hidden danger that the bent section is broken in the uterus as any one section of the bent section has more than two stress points and when the bent section is stressed, it is hard to break the bent section under support by each stress point.

Optionally, the bent groove includes a first bent unit and a second bent unit that are connected, the first bent unit being a dovetail groove or a trapezoidal groove and the second bent unit being a dovetail groove or a trapezoidal groove, too.

By adopting the technical scheme, single arrangement and combined arrangement of the dovetail groove and the trapezoidal groove can enable the periphery of the bent section to be formed with stress points. When the bent section twists as the rotary inner tube rotates, it is convenient to improve the strength of the bent section and to reduce a condition that the bent section is broken due to twisting.

Optionally, the first bent unit and the second bent unit are both dovetail grooves, and the dovetail groove of the first bent unit is arranged in a forward direction, the dovetail groove of the second bent unit is arranged in a reverse direction, and an end portion of one end of the dovetail groove of the first bent unit is connected with an end portion of one end of the dovetail groove of the second bent unit.

By adopting the technical scheme, the bent groove is formed by connecting the forward and reverse dovetail grooves one by one, which is a better structure of increasing the quantity of the stress points of the bent section, so that it is convenient to reduce the hidden danger of breaking the bent section.

Optionally, the handle mechanism includes a handheld handle, a valve core assembly located in the handheld handle, a water inlet and outlet assembly mounted on the handheld handle and a rotary knob assembly rotatably connected with the handheld handle; the valve core assembly includes a water outlet inner tube and a water inlet outer tube, and the water inlet outer tube is fixed in the handheld handle and is sleeved in the circumferential direction of the water outlet inner tube; one end of the water outlet inner tube is connected with the rotary knob assembly and the other end of the water outlet inner tube is connected with the rotary inner tube; and the water inlet and outlet assembly is communicated with the valve core assembly.

By adopting the technical scheme, the rotary knob assembly rotates to drive the water outlet inner tube to rotate so as to drive the rotary inner tube to rotate. As the water inlet and outlet assembly is connected with the water inlet outer tube and the water inlet outer tube is fixed to the handheld handle and dos not rotate along with the water outlet inner tube, a problem that the water outlet assembly is pulled cut as the water inlet outer tube rotates infinitely.

Optionally, the intubation mechanism further includes a soft wrapper, the soft wrapper wraps the outer side of the supporting outer tube, the inner side of the rotary inner tube is a water suction channel, and a washing water inlet channel is arranged between the rotary inner tube and the supporting outer tube; the water outlet inner tube is communicated with the interior of the rotary inner tube and the water inlet outer tube is connected with the supporting outer tube; and the water inlet and outlet assembly includes a water inlet pipeline and a water outlet pipeline, the water inlet pipeline is communicated with the water inlet outer tube, and the water outlet pipeline is communicated with the water outlet inner tube.

By adopting the technical scheme, the supporting outer tube is connected with the water inlet outer tube, so that the supporting outer tube can be prevented from rotating along with the rotary inner tube. As the straight line section of the supporting outer tube is kept immobile when the rotary inner tube rotates, the soft wrapper is also kept immobile, so that friction between the soft wrapper and the inner walls of the uterus and the vagina, and therefore, pain of a patient can be reduced. The soft wrapper is generally soft and is not too cold to be contacted with a human body, so that it is convenient to reduce discomfort of the human body. Washing water can enter the uterus via a washing water inlet channel between the rotary inner tube and the supporting outer tube, so that the uterus is kept in a plump state, and it is convenient to reduce collision between the bent portion of the rotary inner tube and the inner wall of the uterus when the rotary inner tube is rotated. The washing water further can wash the lens of the camera conveniently, and a condition that impurities such as blood streaks in the uterus pollute the lens of the camera is reduced, so that it is convenient to improve the cleanliness of the lens of the camera. Sewage after washing in the uterus can flow back to the water outlet inner tube via a water suction channel and is discharged via a water outlet pipeline, so that an inlet and outlet circulation of the washing water in the uterus is formed.

Optionally, the water outlet inner tube is circumferentially connected with two plugging rings, and an outer wall of each of the plugging rings and an inner wall of the water inlet outer tube are hermetically arranged and are rotatably connected; the water outlet inner tube is provided with a water outlet located below the two plugging rings, the end of the rotary inner tube away from a camera is plugged, and the rotary inner tube is provided with a water outlet hole corresponding to the water outlet; the water inlet pipeline is connected with the water inlet outer tube, and the water inlet pipeline is located between the supporting outer tube and the plugging ring close to the supporting outer tube; and the water outlet inner tube is connected with the water inlet outer tube, and the water outlet inner tube is located between the two plugging rings.

By adopting the technical scheme, the plugging rings are arranged to divide the interior of the water inlet outer tube into two independent spaces, a water outlet space can be formed between the two plugging rings, and a water inlet space can be formed between the supporting outer tube and the plugging ring close to the supporting outer tube, so that it is convenient to separate inlet and outlet lines of the washing water in the water inlet outer tube. The cleaned washing water in the water inlet pipeline enters the washing water inlet channel via the gap between the supporting outer tube and the rotary inner tube, the sewage in the uterus enters the rotary inner tube, flows axially along the rotary inner tube, enters the water outlet inner tube via the water outlet hole, enters the water outlet space of the water inlet outer tube between the two plugging pieces via the water outlet and finally flows out via the water outlet pipeline. An effect that the washing water comes in and goes out under a condition that the rotary inner tube rotates and the supporting outer tube does not rotate is obtained.

Optionally, the side of the rotary inner tube away from the handle mechanism is provided with a mounting plate and a mounting hood, the camera and an LED lamp are arranged on the side of the mounting plate away from the handle mechanism, the camera and the mounting hood are provided in such a way that cover the circumferential direction of the mounting plate and the camera and the LED lamp are sealed, and the mounting hood is made from a transparent material; and the mounting plate and the mounting hood are provided with avoidance holes at the washing water inlet channel and the water suction channel.

By adopting the technical scheme, the mounting plate is used for fixing the camera and the LED lamp, and the mounting hood is matched with the mounting plate to seal the camera and the LED lamp, so that a condition that the washing water soaks the camera and the LED lamp is reduced. The LED lamp illuminates the surrounding environment of the camera via the mounting hood, and the camera monitors conditions in the uterus via the mounting hood. The washing water entering the uterus is closer to the camera to wash the mounting hood timely, so that a condition that the monitoring effect of the camera is affected as impurities such as blood steaks in the uterus cover the mounting hood is reduced. The water suction channel is used for flowing sewage after the uterus is cleaned back, so that the clean washing water can enter the uterus continuously and wash the uterus.

Optionally, the rotary knob assembly further includes a rotary knob, a first limiting ring and a second limiting ring that are arranged successively, the end of the rotary knob stretching into the handheld handle is connected with the first limiting ring, and the first limiting ring is connected with the water outlet inner tube; the second limiting ring is sleeved on the outer side of the water outlet inner tube and is located between the water inlet outer tube and the first limiting ring; the first limiting ring is provided with a first limiting block, the water inlet outer tube is provided with a second limiting block, a circumferential side wall of the second limiting ring is provided with a first limiting groove and a second limiting groove in a staggered manner, axes of the first limiting groove and the second limiting groove extend along the circumferential direction of the second limiting ring, the first limiting block is embedded into the first limiting groove, and the second limiting block is embedded into the second limiting groove.

By adopting the technical scheme, the rotary knot rotates to drive the first limiting ring and the water outlet inner tube to rotate, so that the rotating angle of the rotary knob can be limited under double limitation of the first limiting block and the first limiting groove as well as the second limiting block and the second limiting groove, and the hidden danger that the line that connects the camera and the LED lamp is pulled out as the water outlet tube rotates infinitely is reduced.

Optionally, the handheld handle is internally provided with a circuit board and a patch cord that are connected electrically, the rotary inner tube is internally provided with a wire outlet tube, the patch cord is arranged in t the wire outlet tube in a penetrating manner, the side of the patch cord away from the circuit board is provided with a Y-shaped portion, and the Y-shaped portion stretches between the mounting plate and the mounting hood; and two end portions of the Y-shaped portion are electrically connected with the LED lamp, and a middle portion of the Y-shaped portion is electrically connected with the camera.

By adopting the technical scheme, the Y-shaped portion is designed, so that the wiring space of the camera and the LED lamp are saved and it is convenient to shorten the distance between the camera and the LED lamp. The camera and the LED lamp as a whole occupy a small space, and it is convenient for the LED lamp to better illuminate the camera.

Optionally, the handheld handle includes a first handheld portion and a second handheld portion, the intubation mechanism, the valve core assembly, the water inlet and outlet assembly and the rotary knob assembly are connected with the first handheld portion, the second handheld portion is detachably connected with the first handheld portion, and the circuit board is mounted in the second handheld portion.

By adopting the technical scheme, as the uterine endoscope is a disposal utensil, in consideration of sanitation, it is needed to abandon all the structures directly or indirectly contacted with patients. The handle portion is separated into the first handheld portion and the second handheld portion, so that it is convenient to recycle the circuit board, and therefore, the resource utilization ratio is improved. The recycled circuit board can be directly separated from the original first handheld portion via the second handheld portion and is conveniently connected with the clean first handheld portion.

BENEFICIAL EFFECTS OF INVENTION

Beneficial Effects

In conclusion, the application includes at least one beneficial technical effect below:

1. By arranging the spirally arranged continuous bent groove on the bent section, an effect of reducing the medical hidden danger that the bent section is broken in the uterus is gained.

2. By arranging the handheld handle, the valve core assembly, the water inlet and outlet assembly and the rotary knob assembly, an effect of being convenient for the washing water to come in and go out of the uterus while driving the rotary inner tube to rotate is gained, and a monitoring effect of the uterine endoscope is improved.

3. By arranging the circuit board, the patch cord and the LED lamp, effects that the wiring space of the camera and the LED lamp are saved and the camera and the LED lamp as a whole occupy a small space can be gained.

BRIEF DESCRIPTION OF THE DRAWINGS

Description of the Drawings

Figure 1:
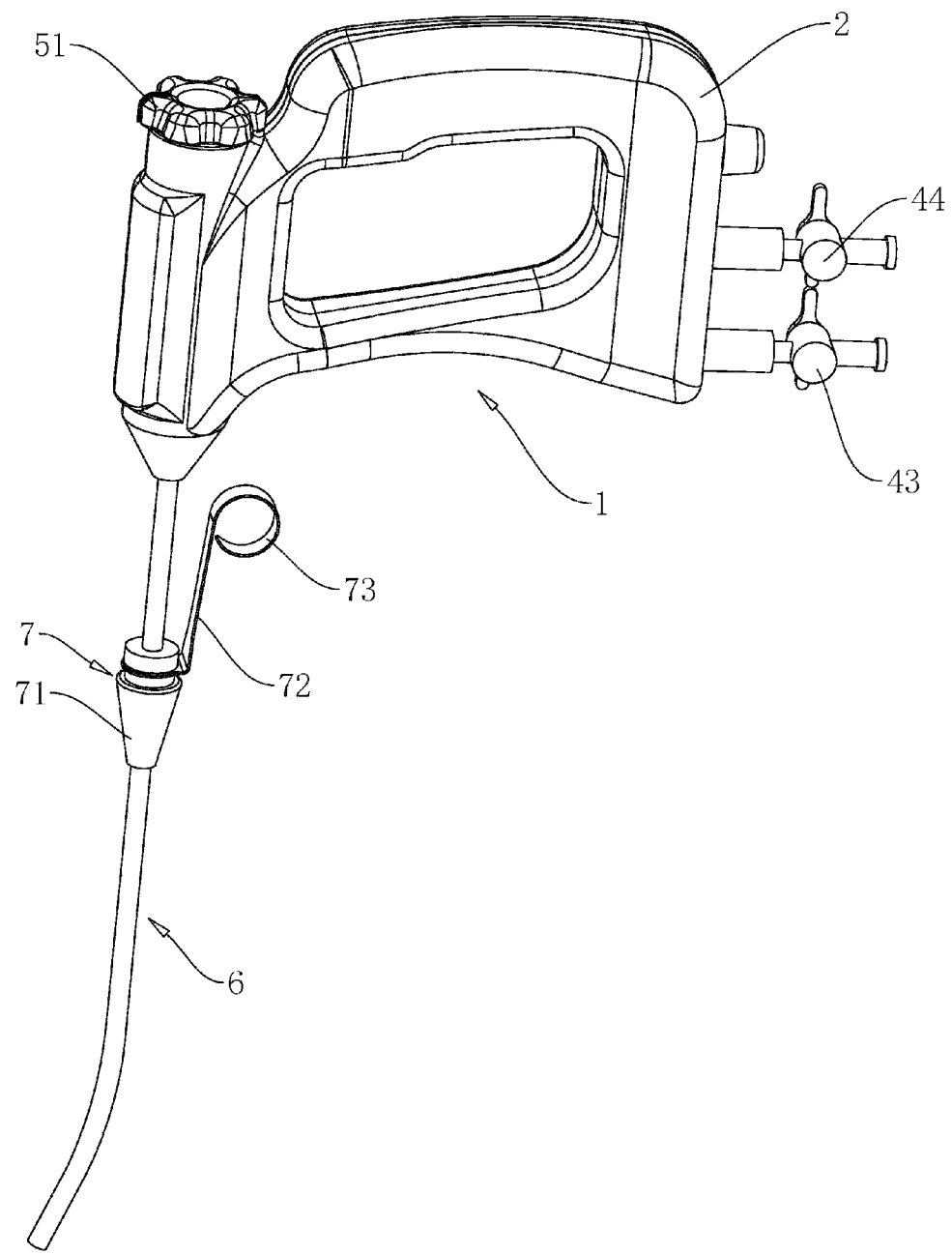

FIG. 1 is a schematic diagram of an overall structure of a uterine endoscope of an embodiment 1 of the application.

Figure 2:
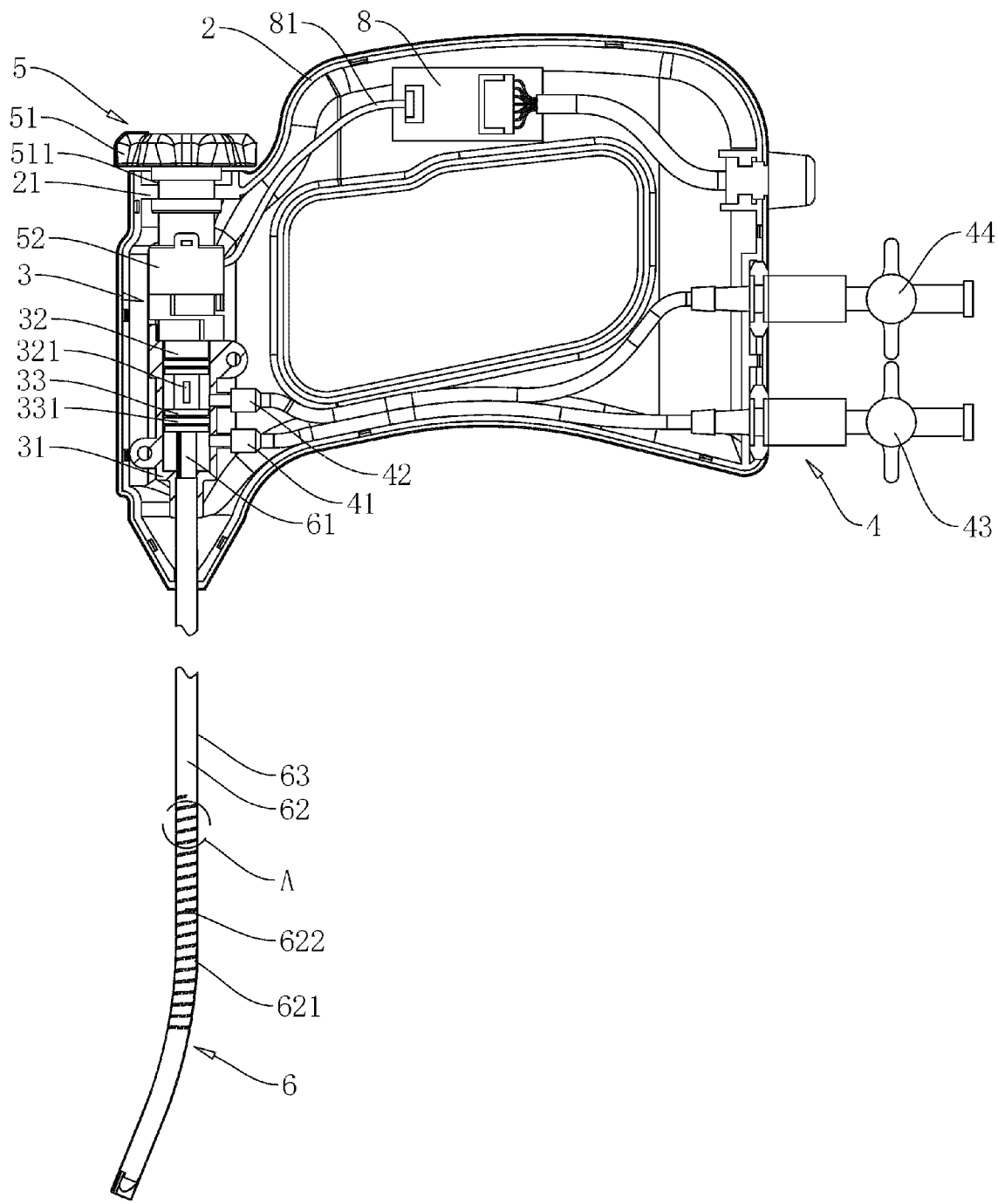

FIG. 2 is a schematic diagram of a section structure of a uterine endoscope of an embodiment 1 of the application.

Figure 3:
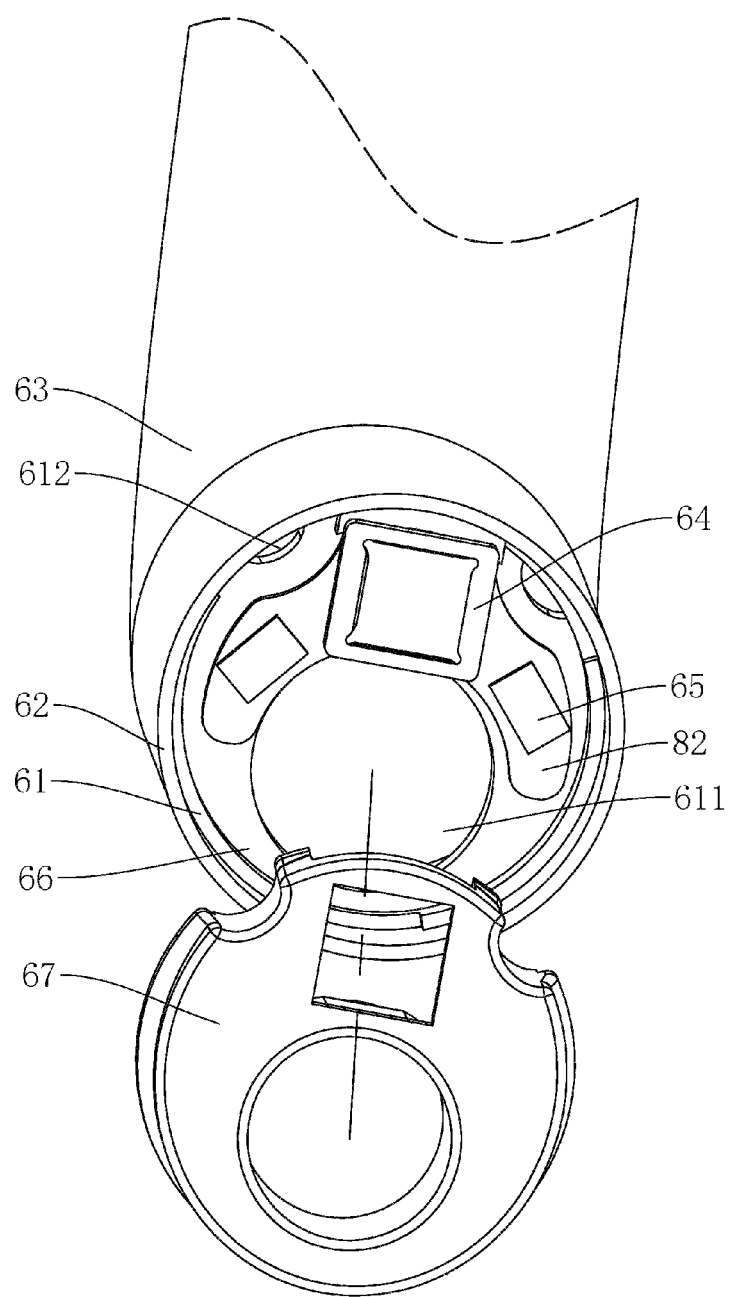

FIG. 3 is a schematic diagram of an exploded structure of a mounting hood and a mounting plate of an embodiment 1 of the application.

Figure 4:
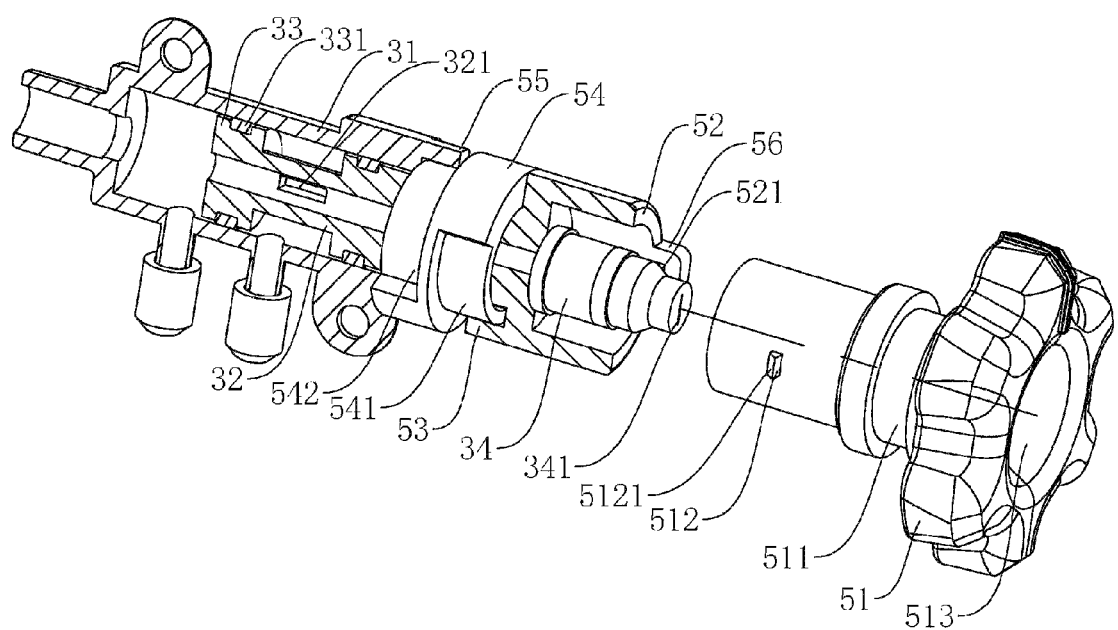

FIG. 4 is a schematic diagram of an exploded structure of a rotary knob and a valve core assembly of an embodiment 1 of the application.

Figure 5:
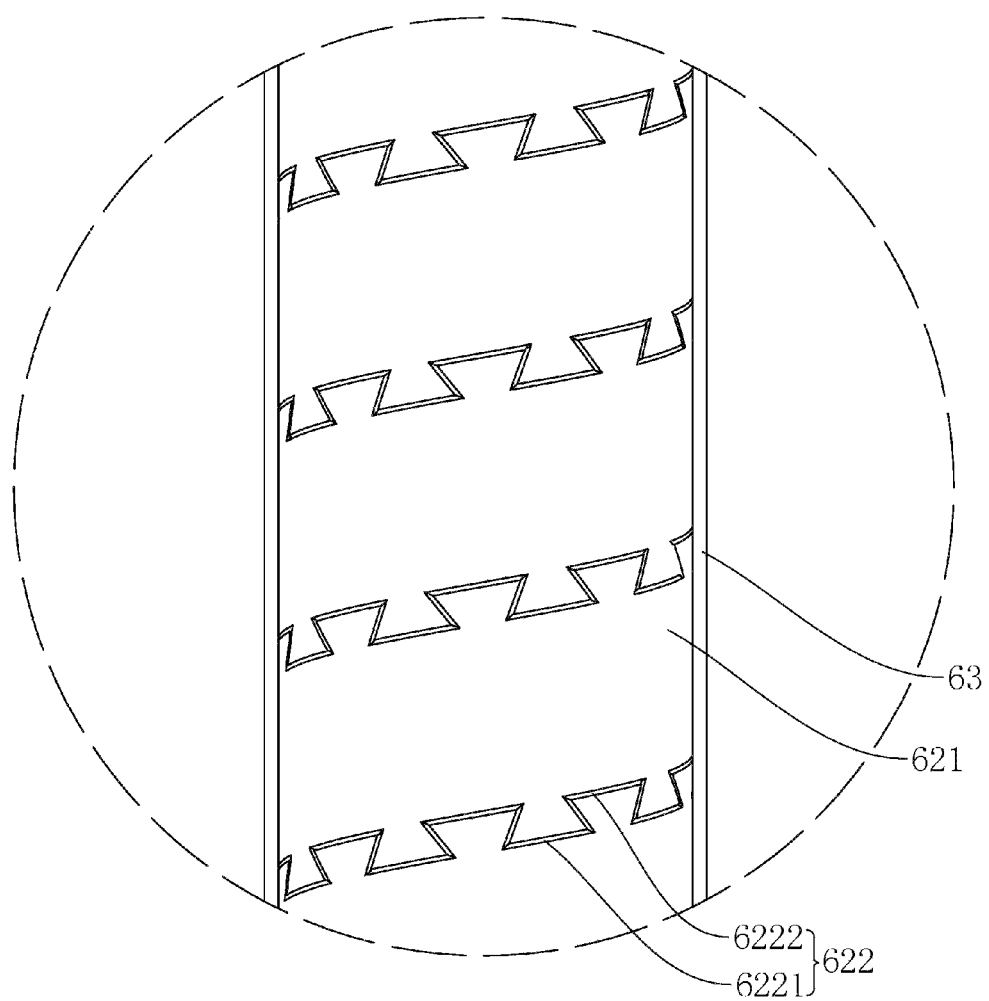

FIG. 5 is a schematic diagram of a partial enlarged structure of A in the FIG. 2.

Figure 6:
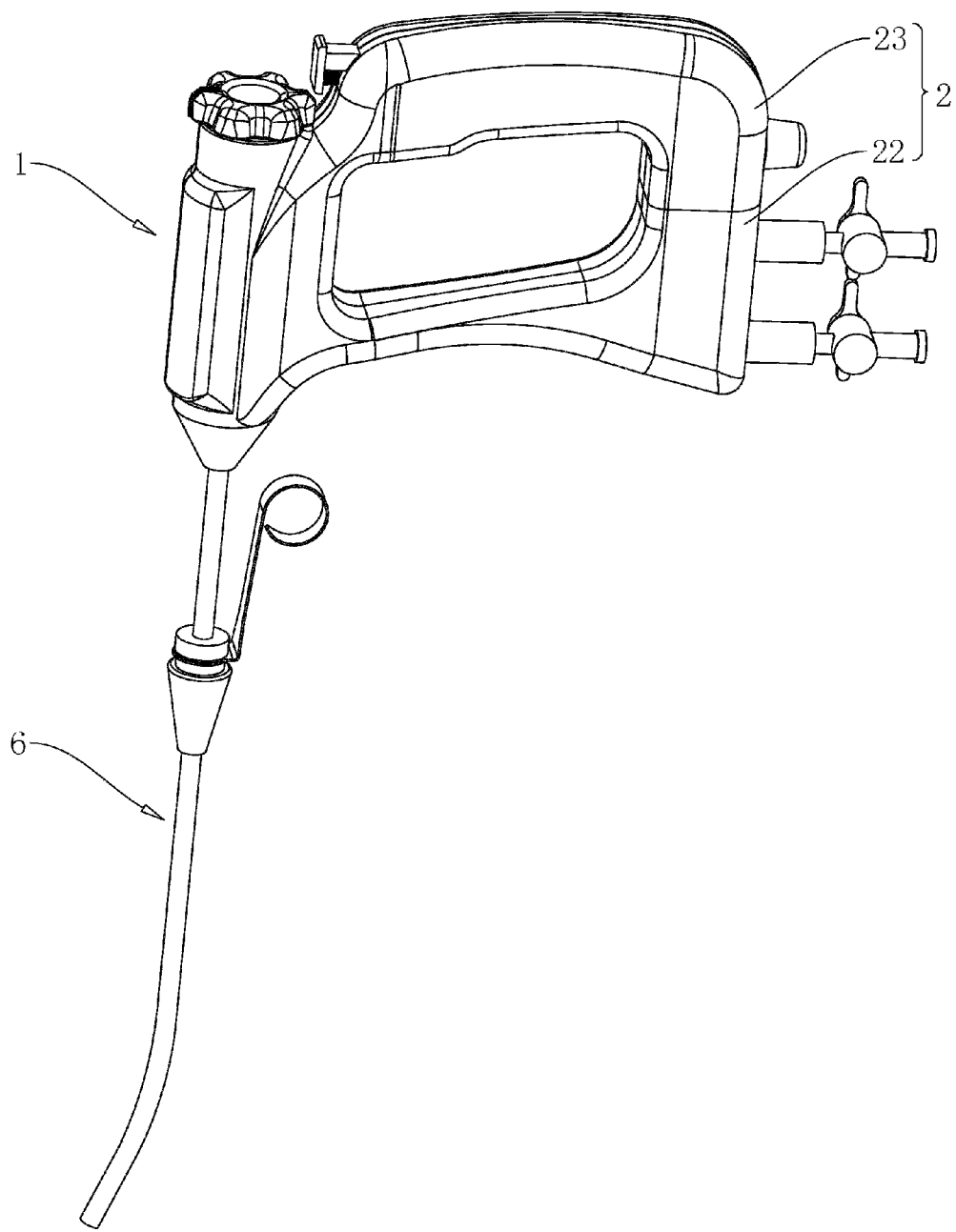

FIG. 6 is a schematic diagram of an overall structure of a uterine endoscope of an embodiment 2 of the application.

Figure 7:
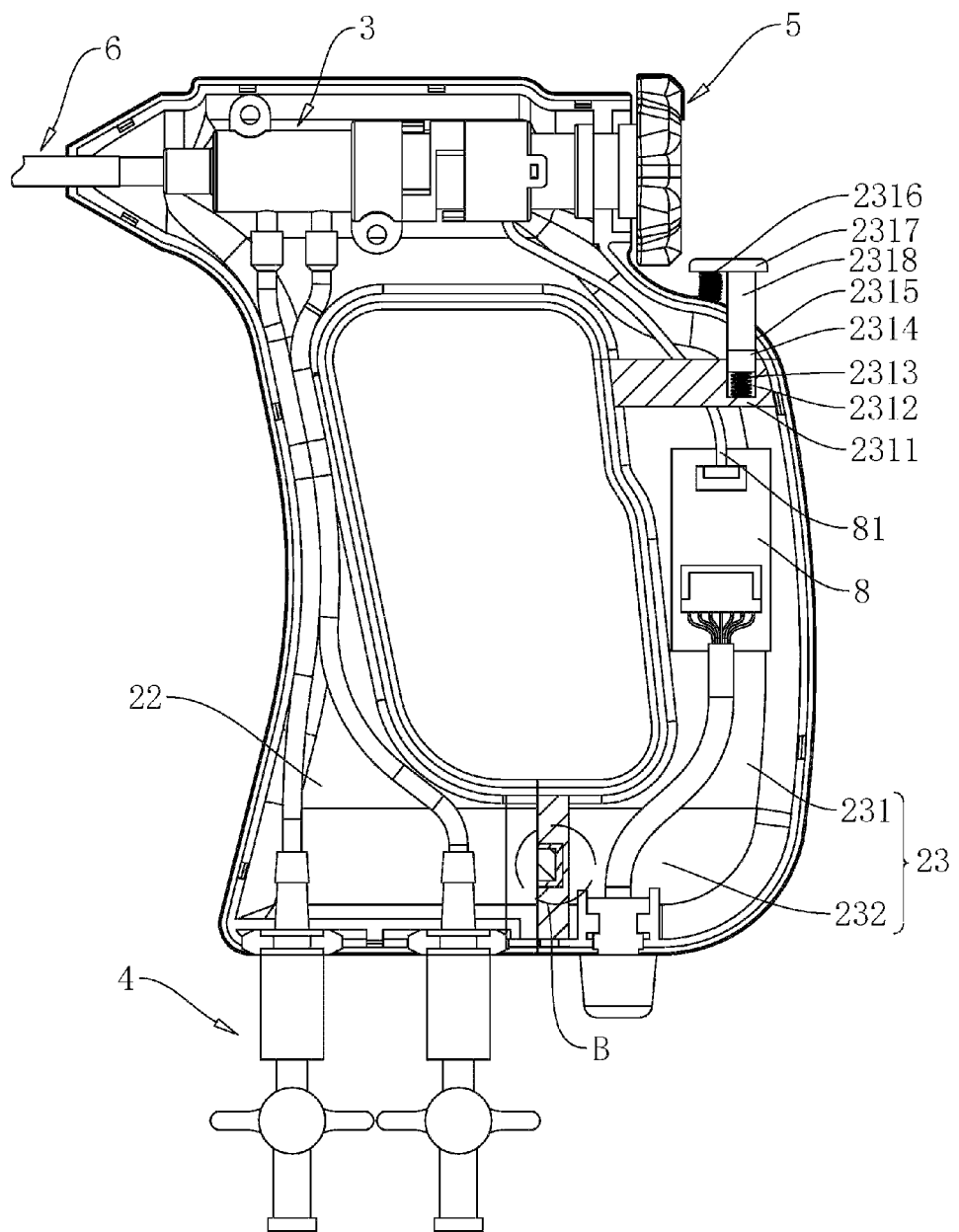

FIG. 7 is a schematic diagram of a section structure of an uterine endoscope of an embodiment 2 of the application.

Figure 8:
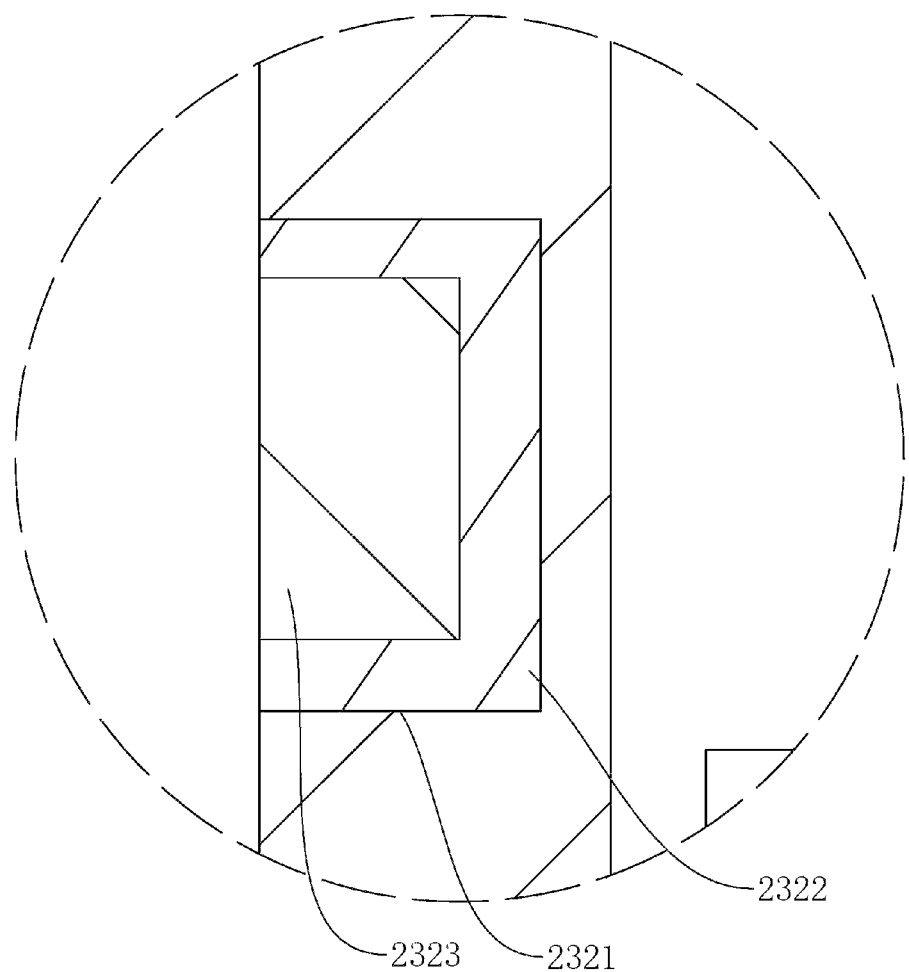

FIG. 8 is a schematic diagram of a partial enlarged structure of B in the FIG. 7.

DETAILED DESCRIPTION

Best Embodiment for Applying the Invention

Best Embodiment of the Invention

Further description of the application will be made below in combination with FIGS. 1-8.

The embodiment of the application discloses a disposable uterine endoscope. Referring to FIG. 1, a disposable uterine endoscope includes a handle mechanism 1 and an intubation mechanism 6. The handle mechanism 1 is handheld by an operator, and the intubation mechanism 6 is used for being inserted into a vagina and an uterus of a human body to peep and examine the environment in the uterus.

Referring to FIG. 2 and FIG. 3, the handle mechanism 1 includes a handheld handle 2, a valve core assembly 3 located in the handheld handle 2 and a water inlet and outlet assembly 4 mounted on the handheld handle 2. The intubation mechanism 6 includes a rotary inner tube 61, a supporting outer tube 62 connected outside the rotary inner tube 61 in a sleeving manner and a soft wrapper 63 connected outside the supporting outer tube 62 in a sleeving manner. The valve core assembly 3 includes a water inlet outer tube 31 and a water outlet inner tube 32 inserted into the water inlet outer tube 31, the water outlet inner tube 32 and the water inlet outer tube 31 are arranged coaxially, and the water inlet outer tube 31 is fixed in the handheld handle 2 via a screw. One end of the rotary inner tube 61 is inserted into the water outlet inner tube 32 and the other end of the rotary inner tube 61 is provided with a bending portion, a bending angle of the bending portion is about 22° and a head of the bending portion is provided with a camera 64. One end of the supporting outer tube 62 is inserted into the water inlet outer tube 31 and the other end of the supporting outer tube 62 extends to the side of the rotary inner tube 61 provided with the camera 64. The water inlet and outlet assembly 4 includes a water inlet pipeline 41 and a water outlet pipeline 42, wherein the water inlet pipeline 41 is communicated with the water inlet outer tube 31 and the water outlet pipeline 42 is communicated with the water outlet inner tube 32. The water inlet pipeline 41 introduces clean washing water into the water outlet inner tube 32, and the washing water enters the uterus via the gap between the rotary inner tube 61 and the supporting outer tube 62, so that the uterus is kept in a dilated state for the convenience of examination. Sewage containing blood steaks and impurities in the uterus can flow back to the water outlet inner tube 32 via the rotary inner tube 61 and is discharged from the water outlet pipeline 42.

Referring to FIG. 2 and FIG. 4, in order to make inlet and outlet loops of the washing water not interfere with each other in the valve core assembly 3, the periphery of the water outlet inner tube 32 is connected with two plugging rings 33, and the outer walls of the plugging rings 33 and the inner wall of the water inlet outer tube 31 are hermetically arranged and are rotatably connected. The circumferential side wall of the plugging ring 33 is provided with the mounting groove, the seal ring 331 is embedded into the mounting groove, and the two seal rings 331 divide the interior of the water inlet outer tube 31 into two independent spaces, that is, the space between the two seal rings 331 are water outlet spaces, and the space between the seal ring 331 on the side close to the supporting outer tube 62 and the soft wrapper 63 is the water inlet space, so that it is convenient to separate lines of the washing water that comes in and goes out in the water inlet outer tube 31.The end of the water outlet inner tube 32 away from the camera 64 is provided with a rubber plug 34 to plug the rotary inner tube 61.A section of peripheral wall of the rotary inner tube 61 stretching into the water outlet inner tube 32 is provided with a water outlet hole, and the water outlet hole is located between the two plug rings 33. The water outlet inner tube 32 is provided with the water outlet 321 between the plugging rings 33 and the water outlet hole and the water outlet 321 are formed correspondingly. The water inlet pipeline 41 and the water outlet pipeline 42 are both connected with the water inlet outer tube 31, the water inlet pipeline 41 is located between the supporting outer tube 62 and the plugging ring 33 close to the supporting outer tube 62, and the water outlet inner tube 32 is located between the plugging rings 33.

Referring to FIG. 2 and FIG. 3, the inner side of the rotary inner tube 61 is the water suction channel 611, and the washing water inlet channel 612 is arranged between the rotary inner tube 61 and the supporting outer tube 62. The washing water enters the water inlet outer tube 31 via the water inlet pipeline 41 and enters the uterus via the washing water inlet channel 612. When entering the uterus, it further can wash the lens of the camera 64, so that the lens of the camera 64 is kept with a clear sight of view all the time. Sewage in the uterus flows back to the water outlet inner tube 32 via the water suction channel 611, enters the water inlet outer tube 31 via the water outlet 321, and then flows out via the water outlet pipeline 42. As the seal rings 331 are arranged, the washing water and the sewage are located in different sealed spaces in the water inlet outer tube 31 without mutual interference.

Referring to FIG. 2, the water inlet and outlet assembly 4 further includes a water inlet valve 43 and a water outlet valve 44. The water inlet valve 43 and the water outlet valve 44 are mounted on the handheld handle 2 and are located outside the handheld handle 2, the water inlet valve 43 is communicated with the water inlet pipeline 41, and the water outlet valve 44 is communicated with the water outlet pipeline 42. The washing water can be controlled to come in and go out and the flow of the washing water that comes in and goes out can be controlled by adjusting on-off of the water inlet valve 43 and the water outlet valve 44, so that it is of better adaptability.

Referring to FIG. 2 and FIG. 4, the handle mechanism 1 further includes a rotary knob assembly 5 rotatably connected with the handheld handle 2. The rotary knob assembly 5 further includes a rotary knob 51, a first limiting ring 52 and a second limiting ring 54 arranged successively, wherein the circumferential wall of the rotary knob 51 is provided with the rotating groove 511, the inner wall of the handheld handle 2 is connected with the mounting ring 21, the mounting ring 21 and the water outlet inner tube 32 are arranged coaxially, and the side of the rotary knob 51 provided with the mounting ring 21 stretches into the handheld handle 2 and the mounting ring 21 is embedded into the rotating groove 511. The mounting ring 21 and the rotating groove 511 are arranged to limit the axial position of the rotary knob 51, and it is convenient to rotatably connect the rotary knob 51 and the handheld handle 2. The width of the mounting ring 21 in the embodiment is smaller than that of the rotating groove 511, and when the mounting ring 21 is embedded into the rotating groove 511, the rotating groove 511 can provide the mounting ring 21 with an axial tuning space.

Referring to FIG. 2 and FIG. 4, the limiting ring 52 is located on the side of the water outlet inner tube 32 facing the rotary knob 51, the first limiting ring 52 and the water outlet inner tube 32 are integrally formed, and the side of the rotary knob 51 facing the first limiting ring 52 is inserted into the first limiting ring 52. The circumferential wall of the rotary knob 51 is connected with mounting lugs 512 symmetrically arranged along the axis of the rotary knob 51, and the outer wall of each mounting lugs 512 is a bevel 5121. Assuming that the distance between the end of the bevel 5121 facing the first limiting ring 52 and the outer wall of the rotary knob 51 is a and the distance between the end of the bevel 5121 away from the first limiting ring 52 and the outer wall of the rotary knob 51 is b, a is smaller than b. The side of the first limiting ring 52 facing the rotary knob 51 is connected with the mounting lugs 56 symmetrically arranged along the axis of the first limiting ring 52, and each of the mounting lugs 56 is provided with a mounting hole 521 formed in the wall of the mounting lug 56. When the rotary knob 51 is inserted into the first limiting ring 52, the mounting lug 512 guided by the bevel 5121 extrudes the mounting lug 56 gradually and is finally embedded into the mounting hole 521. The rotary knob 51 rotates to drive the first limiting ring 52 and the water outlet inner tube 32 to rotate, and the water outlet inner tube 32 rotates to make the rotary inner tube 61 rotate at the same time.

Referring to FIG. 2 and FIG. 4, the second limiting ring 54 is arranged on the peripheral outer side of the water outlet inner tube 32 in a sleeving manner and is located between the first limiting ring 52 and the water inlet outer tube 31. The circumferential side wall of the second limiting ring 54 is provided with the first limiting groove 541 and the second limiting groove 542. The first limiting groove 541 is formed close to the first limiting ring 52 and the second limiting groove 542 is formed close to the water inlet outer tube 31. The first limiting groove 541 is formed toward the groove wall on one side of the first limiting ring 52 in a penetrating manner, the first limiting block 53 is integrally formed on the side of the first limiting ring 52 facing the second limiting ring 54, and the first limiting block 53 stretches into the first limiting groove 541 from the side of the first limiting groove 541 facing the first limiting ring 52. The second limiting groove 542 is formed toward the groove wall on one side of the water inlet outer tube 31 in a penetrating manner, the second limiting block 55 is integrally formed on the side of the water inlet outer tube 31 facing the second limiting ring 54, and the second limiting block 55 stretches into the second limiting groove 542 from the side of the second limiting groove 542 facing the water inlet outer tube 31. The first limiting groove 541 and the second limiting groove 542 are arranged in a staggered manner along the circumferential direction of the second limiting ring 54. The rotary knob 51 rotates forwards to drive the first limiting ring 52 to rotate at the same time till the first limiting block 53 abuts against the groove wall on one side of the first limiting groove 541, and at the time, the first limiting ring 52 is rotated continuously to drive the second limiting ring 54 to rotate at the same time. When the side wall of the second limiting ring 54 abuts against the second limiting block 55, the rotary knob 51 is limited. A limiting principle of the rotary knob 51 that rotates reversely is similar to the above. By double limitation of the first limiting block 53 and the second limiting block 55, it is relatively stable to limit forward and reverse rotation of the rotary knob 51. The forward and reverse rotating angles of the rotary knob 51 in the embodiment are 180-350°, so that the rotating angle of the rotary knob 51 can be limited at 220°.

Referring to FIG. 4, one end of the rubber plug 34 in the water outlet inner tube 32 can stretch into the rotary knob 51, an axis of the rotary knob 51 can be provided with the insertion hole 513, and the insertion hole 513 is communicated with the water outlet inner tube 32. One end of the rubber plug 34 is a through hole and the other end of the rubber plug 34 is provided with a mounting gap 341, and the mounting gap 341 is communicated with the through hole. As the rubber plug 34 is elastic, the mounting gap 341 is in a closed state in a normal state, so that it is convenient for the rubber plug 34 to plug the end of the water outlet inner tube 32 facing the rotary knob 51. When it is necessary to perform an operation in the uterus with biopsy forceps, the biopsy forceps can enter via the insertion hole 513 at the rotary knob 51, then distracts the mounting gap 341 to be inserted into the through hole of the rubber plug 34, then enters the water outlet inner tube 32 and then enters the uterus via the water suction channel 611.

Referring to FIG. 1 and FIG. 2, during uterus examination, it is unnecessary to expand the uterus when apparatuses with the diameters smaller than 5 mm are used. The section of the straight line section of the supporting outer tube 62 is round, the outer diameter of the straight line section of the supporting outer tube 62 is 4.8 mm, the section of the bent section 621 is elliptical, the long axis of the bent section 621 is 4.8 mm and the short axis of the bent section 621 is 4.5 mm. As the diameters of orifices of the uteruses are inconsistent, when the diameter of the orifice of the uterus of a patient is greater, the plugging shaft 7 can be arranged outside the soft wrapper 63 in a sleeving manner to reduce a condition that water in the uterus flows out from the soft wrapper 63. The side of the plugging shaft 7 facing the orifice of the uterus is provided with the conical surface 71, the side of the outer side of the plugging shaft 7 away from the conical surface 71 is connected with the push rod 72, and the end of the push rod 72 away from the pugging shaft 7 is bended as the buckling ring 73. A doctor can hold the handheld handle 2 with one hand and hook the buckling ring 73 with one finger and then push the plugging shaft 7 to the orifice of the uterus, thereby playing a role of holding the handheld handle 2 and plugging the orifice of the uterus with one hand. At the time, the other hand can be used for rotating the rotary knob 51 or placing the biopsy forceps.

Referring to FIG. 2 and FIG. 5, in order to reduce friction between the tabulation mechanism 6 and the vagina so as to reduce pain of the patient, when the rotary inner tube 61 is rotated, the supporting outer tube 62 no longer rotates along with the rotary inner tube 61, so that the outer wall of the bent section 621 is provided with the continuous bent groove 622, and the bent groove 622 is spirally arranged along the circumferential direction of the bent section 621. By arranging the bent groove 622, the bent section 621 is formed with a gap space, through which the bent section 621 stretches and twists, so that the bent section 621 can twist along with rotation of the rotary inner tube 61.

Referring to FIG. 2 and FIG. 5, the bent groove 622 includes the first bent unit 6221 and a second bent unit 6222 that are connected, the first bent unit 6221 is a dovetail groove, a trapezoidal groove or a triangle groove, and the second bent unit 6222 is a dovetail groove or a trapezoidal groove or a triangle groove, too. In the embodiment, the first bent unit 6221 and the second bent unit 6222 are both dovetail grooves, and the dovetail groove of the first bent unit 6221 is arranged in a forward direction, the dovetail groove of the second bent unit 6222 is arranged in a reverse direction, and an end portion of one end of the dovetail groove of the first bent unit 6221 is connected with an end portion of one end of the dovetail groove of the second bent unit 6222 to form the continuous bent groove 622. The shape of the bent groove 622 makes any cross section of the bent section 621 exceeds two connecting points, and the connecting points are stress points of the bent section 621 subjected to the torque, so that the hidden danger that the bent section 621 is broken when twisting.

Referring to FIG. 2 and FIG. 3, the handheld handle 2 is internally provided with a circuit board 8 and a patch cord 81 connected electrically, the circuit board 8 is fixed in the handheld handle 2, one end of the patch cord 81 is connected with the circuit board 8 and the other end of the patch cord 81 penetrates through the gap between the supporting outer tube 62 and the rotary inner tube 61 and stretches to the side of the rotary inner tube 61 provided with the camera 64. The patch cord 81 may be an arranged wire for the convenience of waterproofness and wire layout. The side of the patch cord 81 away from the circuit board 8 is provided with a Y-shaped portion 82, two end portions of the Y-shaped portion 82 are connected with an LED lamp 65, and the middle portion of the Y-shaped portion 82 is electrically connected with the camera 64, so that the LED lamp 65 can be closer to the camera 64, thereby facilitating illumination of the camera 64.

Referring to FIG. 2 and FIG. 3, in order to fix the positions of the camera 64 and the LED lamp 65, the side of the rotary inner tube 61 away from the handheld assembly is provided with the mounting plate 66 and the mounting hood 67, the mounting plate 66 plugs the orifice of the rotary inner tube 61, the mounting hood 67 covers the side of the mounting plate 66 away from the rotary inner tube 61, the mounting plate 66 and the mounting hood 67 are provided with avoidance holes in the washing water inlet channel 612 and the water suction channel 611, the Y-shaped portion 82 stretches into the rotary inner tube 61 and is fixed to the mounting plate 66, and the mounting hood 67 plugs the camera 64 and the LED lamp 65. The mounting hood 67 is made from a transparent material which may be either transparent acrylic, or a PC material. In the embodiment, the PC material is used. The mounting plate 66 can fix the Y-shaped portion 82, the camera 64 and the LED lamp 65, so that it is convenient to take pictures stably by the camera 64. The mounting hood 67 can protect the camera 64 and the LED lamp 65, thereby reducing a condition that the washing head soaks the camera 64 and the LED lamp 65.

The implementation principle of the disposable uterine endoscope in the embodiment of the application is as follows: during usage, first, the tabulation mechanism 6 is inserted into the uterus via the vagina, and the length of the tabulation mechanism 6 stretching out of the handheld handle 2 can be set at 200 mm. Then, one finger of the hand of the handheld handle 2 is grasped to buckle the buckling ring 73 and the plugging shaft 7 is pushed to the entrance of the vagina to plug the orifice of the uterus. If the diameter of the orifice of the uterus is smaller, the plugging shaft 7 may not be used. Then, the circuit board 8 is connected with an image processor at the rear end, so that it is convenient to project the picture collected by the camera 64 to an image display after being processed. Then, switches of the water inlet valve 43 and the water outlet valve 44 are turned on manually. In the initial stage, the water inflow of the washing water needs to be greater than the sewage outflow, and when the uterus is filled with the washing water, the water inflow and outflow of the washing water can be controlled to the same amounts.

Then, the rotary inner tube 61 is rotated by adjusting the rotary knob 51 so as to observe conditions in the uterus via the camera 64. The circumferential direction of the rotary knob 51 can be provided with a tick mark for positioning, so that it is convenient for the operator to know the next rotating direction. When the rotary inner tube 61 rotates, the straight line section of the supporting outer tube 62 is immobile, and the bent section 621 twists along with rotation of the bent portion of the rotary inner tube 61. The rotary inner tube 61 can rotate at 220° in the forward direction and at 220° in the reverse direction. As the forward and reverse rotating angles of the rotary inner tube 61 have a superposed range, a monitoring range of the camera 64 covers the sight of view of 360° in the uterus, and a condition that the patch cord 81 is broken as the rotary knob 51 rotates infinitely is avoided. Finally, the biopsy forceps can be inserted from the insertion hole 513 at the rotary knob 51, so that the biopsy forceps enter the uterus via the water suction channel 611 to sample tissues in the uterus.

Embodiment of Invention Embodiment of the Invention

Referring to FIG. 6 and FIG. 7, the embodiment is different from the embodiment 1 that the handheld handle 2 includes a first handheld portion 22 and a second handheld portion 23, wherein the intubation mechanism 6, the valve core assembly 3, the water inlet and outlet assembly 4 and the rotary knob assembly 5 are connected with the first handheld portion 22, and the circuit board 8 structure is mounted in the second handheld portion 23. The first handheld portion 22 and all components connected with the first handheld portion 22 are all needed to be abandoned as they are in contact with the patient directly or indirectly, and the second handheld portion 23 and the circuit board 8 can be directly recycled.

Referring to FIG. 6 and FIG. 7, the second handheld portion 23 includes a vertical portion 231 and a horizontal portion 232 arranged at an angle, and the circuit board 8 is mounted in the vertical portion 231. The side of the vertical portion 231 facing the rotary knob 5 is provided with a first mounting block 2311, the side of the first mounting block 2311 facing the first handheld portion 22 is provided with a first embedding groove 2312, the bottom of the first embedding groove 2312 is connected with a first compression spring 2313, and the side of the first compression spring 2313 away from the bottom of the first embedding groove 2312 is connected with a first limiting column 2314. The side of the first handheld portion 22 corresponding to the first embedding groove 2312 is provided with a limiting hole 2315, and one end of the first limiting column 2314 can be embedded into the limiting hole 2315.

A second compression spring 2316 is connected to the upper side of the first handheld portion 22 above the first mounting block 2311, the end of the second compression spring 2316 away from the first handheld portion 22 is connected with a pressing plate 2317, the side of the pressing plate 2317 facing the first handheld portion 22 is provided with a pressing column 2318, and the pressing column 2318 stretches into the limiting hole 2315. When it is necessary to separate the first handheld portion 22 and the second handheld portion 23, the pressing plate 2317 is pressed, so that the second compression spring 2316 is compressed and the pressing column 2318 pushes the first limiting column 2314 to press towards the first embedding groove 2312, and when the first limiting column 2314 is fully embedded into the first embedding groove 2312, the second handheld portion 23 can be translationally taken out.

Referring to FIG. 7 and FIG. 8, the side of the horizontal portion 232 facing the first handheld portion 22 is provided with a second embedding groove 2321, and the inner wall of the second embedding groove 2321 is connected with a magnet block 2322. The side of the first handheld portion 22 facing the second embedding groove 2321 is provided with a second limiting column 2323, and the second limiting column 2323 can be an iron block or a magnet block, so that when the second limiting column 2323 is inserted into the second embedding groove 2321, the second limiting column 2323 can be magnetically connected with the second embedding groove 2321. The first limiting column 2314 and the limiting hole 2315 limit displacement of the second handheld portion 23 in the horizontal direction, and the second limiting column 2323 and the embedding groove 2321 limit displacement of the second handheld portion 23 in the vertical direction.

The implementing principle of the disposable uterine endoscope in the embodiment of the application is as follows: when the handheld handle 2 is assembled, first, the first limiting column 2314 is pressed, so that the first limiting column 2314 is embedded into the first embedding groove 2312, and the second handheld portion 23 is translated horizontally and the second embedding groove 2321 is aligned with the second limiting column 2323. When the first limiting column 2314 is located in the limiting hole 2315, deformation of the first compression spring 2313 is recovered, such that the first limiting column 2314 stretches into the limiting hole 2315, and at the time, the second limiting column 2323 is also inserted into the second embedding groove 2321, and the vertical direction and the horizontal direction of the second handheld portion 23 are limited. The handheld handle 2 can be split into two halves along a center line. After the first handheld portion 22 and the second handheld portion 23 are assembled, the handheld handle 2 can be split along the center line of the handheld handle 2, and the patch cord 81 in the second handheld portion 23 is connected with the patch cord 81 of the camera 64 in the first handheld portion 22, so that the circuit is communicated, and finally, the two halves of the handheld handle 2 are assembled in a clamped manner integrally.

After the disposable uterine endoscope of the embodiment is used and it is necessary to remove the handheld handle 2, the pressing plate 2317 can be pressed, so that the first limiting column 2314 is embedded into the first embedding groove 2312, and at the time, the second handheld portion 23 can be moved horizontally and the second handheld portion 23 is separated from the first handheld portion 22. Finally, the patch cord 81 is sheared, so that the second handheld portion 23 is thoroughly separated from the first handheld portion 22, the first handheld portion 22 can be abandoned, and the second handheld portion 23 which is disinfected can be connected with a new first handheld portion 22.

The above are preferred embodiments of the application and do not limit the protection scope of the application hereunder. Equivalent changes made according to structure, shape and principle of the application shall fall into the protection scope of the application.

What is claimed is:

1. A disposable uterine endoscope, comprising a handle mechanism and an intubation mechanism, wherein the intubation mechanism comprises a rotary inner tube and a supporting outer tube, and one end of the rotary inner tube is rotatably connected with the handle mechanism and an other end of the rotary inner tube is connected with a camera; the supporting outer tube is sleeved in a circumferential direction of the rotary inner tube, one end of the supporting outer tube is fixedly connected with the handle mechanism and an other end of the supporting outer tube is provided with a bent section; and wherein the bent section is provided with a continuous bent groove, and the bent groove is arranged spirally along a circumferential direction of the bent section, wherein the handle mechanism comprises a handheld handle, a valve core assembly located in the handheld handle, a water inlet and outlet assembly mounted on the handheld handle and a rotary knob assembly rotatably connected with the handheld handle; the valve core assembly comprises a water outlet inner tube and a water inlet outer tube, and the water inlet outer tube is fixed in the handheld handle and is sleeved in a circumferential direction of the water outlet inner tube; one end of the water outlet inner tube is connected with the rotary knob assembly and an other end of the water outlet inner tube is connected with the rotary inner tube; and the water inlet and outlet assembly is communicated with the valve core assembly, wherein the intubation mechanism further comprises a soft wrapper, the soft wrapper wraps an outer side of the supporting outer tube, an inner side of the rotary inner tube is a water suction channel, and a washing water inlet channel is arranged between the rotary inner tube and the supporting outer tube; the water outlet inner tube is communicated with an interior of the rotary inner tube and the water inlet outer tube is connected with the supporting outer tube; and the water inlet and outlet assembly comprises a water inlet pipeline and a water outlet pipeline, the water inlet pipeline is communicated with the water inlet outer tube, and the water outlet pipeline is communicated with the water outlet inner tube.

2. The disposable uterine endoscope according to claim 1, wherein the bent groove comprises a first bent unit and a second bent unit that are connected, the first bent unit is a dovetail groove or a trapezoidal groove and the second bent unit is a dovetail groove or a trapezoidal groove, too.

3. The disposable uterine endoscope according to claim 2, wherein the first bent unit and the second bent unit are both the dovetail grooves, and the dovetail groove of the first bent unit is arranged in a forward direction, the dovetail groove of the second bent unit is arranged in a reverse direction, and an end portion of one end of the dovetail groove of the first bent unit is connected with an end portion of one end of the dovetail groove of the second bent unit adjacent to the first bent unit.

4. The disposable uterine endoscope according to claim 1, wherein the water outlet inner tube is circumferentially connected with two plugging rings, and an outer wall of each of the plugging rings and an inner wall of the water inlet outer tube are hermetically arranged and are rotatably connected; the water outlet inner tube is provided with a water outlet located below the two plugging rings, the end of the rotary inner tube away from a camera is plugged, and the rotary inner tube is provided with a water outlet hole corresponding to the water outlet; the water inlet pipeline is connected with the water inlet outer tube, and the water inlet pipeline is located between the supporting outer tube and the plugging ring close to the supporting outer tube; and the water outlet inner tube is connected with the water inlet outer tube, and the water outlet inner tube is located between the two plugging rings.

5. The disposable uterine endoscope according to claim 1, wherein a side of the rotary inner tube away from the handle mechanism is provided with a mounting plate and a mounting hood, the camera and an LED lamp are arranged on a side of the mounting plate away from the handle mechanism, the camera and the mounting hood are provided in such a way that cover a circumferential direction of the mounting plate, the camera and the LED lamp are sealed, and the mounting hood is made from a transparent material; and the mounting plate and the mounting hood are provided with avoidance holes at the washing water inlet channel and the water suction channel.

6. The disposable uterine endoscope according to claim 1, wherein the rotary knob assembly further comprises a rotary knob, a first limiting ring and a second limiting ring that are arranged successively, an end of the rotary knob stretching into the handheld handle is connected with the first limiting ring, and the first limiting ring is connected with the water outlet inner tube; the second limiting ring is sleeved on an outer side of the water outlet inner tube and is located between the water inlet outer tube and the first limiting ring; the first limiting ring is provided with a first limiting block, the water inlet outer tube is provided with a second limiting block, a circumferential side wall of the second limiting ring is provided with a first limiting groove and a second limiting groove in a staggered manner, axes of the first limiting groove and the second limiting groove extend along a circumferential direction of the second limiting ring, the first limiting block is embedded into the first limiting groove, and the second limiting block is embedded into the second limiting groove.

7. The disposable uterine endoscope according to claim 5, wherein the handheld handle is internally provided with a circuit board and a patch cord that are connected electrically, the rotary inner tube is internally provided with a wire outlet tube, the patch cord is arranged in t the wire outlet tube in a penetrating manner, the side of the patch cord away from the circuit board is provided with a Y-shaped portion, and the Y-shaped portion stretches between the mounting plate and the mounting hood; and two end portions of the Y-shaped portion are electrically connected with the LED lamp, and a middle portion of the Y-shaped portion is electrically connected with the camera.

8. The disposable uterine endoscope according to claim 7, wherein the handheld handle comprises a first handheld portion and a second handheld portion, the intubation mechanism, the valve core assembly, the water inlet and outlet assembly and the rotary knob assembly are connected with the first handheld portion, the second handheld portion is detachably connected with the first handheld portion, and the circuit board is mounted in the second handheld portion.

* * * * *